(12) United States Patent
Mukherjee et al.

(10) Patent No.: US 7,737,183 B2
(45) Date of Patent: Jun. 15, 2010

(54) β-AMYLOID AND NEUROFIBRILLARY TANGLE IMAGING AGENTS (75) Inventors: Jogeshwar Mukherjee, Irvine, CA (US); Elizabeth Head, Irvine, CA (US); Crystal Wang, La Palma, CA (US); Pooja C. Patel, Stockton, CA (US)

(73) Assignee: The Regents of the University of California, Oakland, CA (US)

( * ) Notice: Subject to any disclaimer, the term of this patent is extended or adjusted under 35 U.S.C. 154(b) by 142 days.

(21) Appl. No.: 11/873,941

(22) Filed: Oct. 17, 2007

(65) Prior Publication Data

US 2009/0004107 A1    Jan. 1, 2009

Related U.S. Application Data (60) Provisional application No. 60/852,505, filed on Oct. 17, 2006.

(51) Int. Cl.
*A61K 31/13* (2006.01)
*C07C 255/00* (2006.01)

(52) U.S. Cl. ...................... 514/579; 558/409

(58) Field of Classification Search ............... 558/409; 514/579
See application file for complete search history.

(56) References Cited

U.S. PATENT DOCUMENTS

| | | | |
|---|---|---|---|
| 6,274,119 B1 * | 8/2001 | Barrio et al. | 424/1.81 |
| 6,589,504 B1 | 7/2003 | Raub | |
| 6,660,530 B2 | 12/2003 | Barrio | |
| 7,173,061 B2 | 2/2007 | Bouvet | |
| 2005/0048000 A1 | 3/2005 | Gervais | |
| 2007/0053831 A1 | 3/2007 | Barrio | |

FOREIGN PATENT DOCUMENTS

| | | |
|---|---|---|
| WO | 2007033080 | 3/2007 |
| WO | 2007035405 | 3/2007 |

OTHER PUBLICATIONS

Ryu, et al., Curcumin and Dehydrozingerone Derivatives: Synthesis, Radiolabeling, and Evaluation for B-Amyloid Plaque Imaging, J. Med. Chem., 2006, 49, 6111-6119.

Patel et al., F-Fluoropropyl curcumin: A potential PET tracer for imaging inflammation and AB-Plaques, The Journal of Nuclear Medicine, 2007, No. 48 (Supplement 2).

Jogeshwar et al., Radiotracers for a multi-target approach to the diagnosis of Alzheimer's disease, Journal of Labelled Compounds and Radiopharmaceuticals, 2007, pp. 375-379, vol. No. 50, Wiley InterScience.

* cited by examiner

*Primary Examiner*—Rei-tsang Shiao
(74) *Attorney, Agent, or Firm*—Fish & Associates, PC (57) ABSTRACT

Compounds, compositions and methods are contemplated in which senile plaques and/or neurofibrillary tangles are labeled using compounds with improved permeability across the blood brain barrier and improved selective binding to senile plaques and/or neurofibrillary tangles. Contemplated compounds are derivatives of FDDNP or curcumin, which most preferably have improved solubility in aqueous solvents. Labeling is typically performed using a PET detectable label, and especially $^{11}C$ and $^{18}F$.

12 Claims, 3 Drawing Sheets

Ctx: Cortex; Hp: Hippocampus; Cb: Cerebellum
St: Striata; Th: Thalamus; Bs: Brain Stem
FC: Frontal cortex; CA1/Sub Subiculum

10 μM
BRAIN SECTIONS

18F-FPCUR
TOTAL BINDING

HP - Hippocampus; CB - Cerebellum
FC - Frontal Cortex

β-AMYLOID AND NEUROFIBRILLARY TANGLE IMAGING AGENTS

This application claims the benefit of our U.S. provisional patent application with the Ser. No. 60/852,505, which was filed on Oct. 17, 2006, and which is incorporated by reference herein.

This invention was made with Government support under Grant No. AG016573, awarded by the National Institutes of Health. The Government has certain rights in this invention.

FIELD OF THE INVENTION

The field of the invention is imaging agents, and especially imaging agents for neural tissues.

BACKGROUND OF THE INVENTION

A definitive diagnosis of the neurodegenerating Alzheimer's disease has been a goal since the disease was first described in 1906. Alzheimer's disease affects 10% of people older than 65 and is characterized by a progressive loss of cognitive function with an abnormal accumulation of β-amyloid senile plaques and neurofibrillary tangles in the brain as its hallmarks. Alzheimer's disease appears to be caused by the misassembly of the β-amyloid peptide, which is a 39-43 amino acid fragment derived from the amyloid precursor protein. This accumulation of these large extracellular aggregates of amyloid β-peptide onto a β-sheet structure forms the senile plaques characteristic of Alzheimer's patients. Histochemical detection of the senile plaques can be carried out using a variety of compounds that can bind to β-sheets. Similarly, neurofibrillary tangles are intracellular structures that are primarily composed of a misfolded protein called tau, which can also be detected by histochemical stains. Unfortunately, these histochemical stains are not suitable for use in living patients since these stains lack significant ability to cross the blood-brain barrier. Moreover, even if such agents could cross the blood-brain barrier, non-radiological detection would be very difficult. Therefore, it is desirable to develop radiotracers to detect the plaque and tangle binding sites, and the most desirable manner of detection is positron emission tomography (PET).

PET is a non-invasive test that helps physicians diagnose abnormalities, determine the extent of disease, prescribe treatment, and/or track progress in therapeutic intervention. Among other advantages, PET allows imaging of biochemical processes of the body well in advance of anatomical changes associated with abnormal physiological states (i.e., cancer, Alzheimer's, etc). In its most common form, PET scans provide images of tissue activity by measuring decay of positrons from a positron-emitting radiopharmaceutical to thereby locates and quantify "hot spots" for tissue activity related to the specific radiotracer.

Imaging agents using PET can therefore greatly enhance chances of early diagnosis of Alzheimer's disease, which then allows patients to obtain the best therapy and most efficient therapeutic drugs early in the disease progression. Development of imaging agents that detect the senile plaques associated with Alzheimer's disease is currently underway. For example, one class of PET imaging agents comprises selected aminonaphthalene backbones, which have been shown to target the polymeric form of the β-amyloid peptide associated with senile plaques and bind to neurofibrillary tangles. One radiofluorinated molecular imaging probe, 2-(1-{6-[(2-[$^{18}$F]fluoroethyl)(methyl)amino]-2-naphtyl}ethylidene)malonitrile, also known as [$^{18}$F]FDDNP, became the first diagnostic tool to relatively specifically image plaques and tangles (see e.g., U.S. Pat. Nos. 6,274,119 and 6,660,530). Further related compounds are described in U.S. Pat. App. No. 2007/0053831. However, [$^{18}$F]FDDNP is highly lipophilic and consequently exhibits some nonspecific binding. Therefore, the results obtained from PET scans using [$^{18}$F]FDDNP are often relatively poor in image quality and make diagnosis difficult.

Still other known labeling compounds include numerous substituted and radiolabeled benzofuran compounds as described, for example, in U.S. Pat. No. 7,173,061, and numerous substituted quinolinehydrazones as described, for example, in U.S. Pat. No. 6,589,504. Various substituted phenyl imidazo[1,2-b]pyridazine and similar structures are described as imaging agents in WO 2007/033080, and selected substituted benzathiazole compounds are known for labeling and are described in WO 2007/035405. Still further known compounds with more or less specific binding to amyloid are referred to in U.S. Pat. App. No. 2005/0048000. However, and similarly to FDDNP, such known compounds are often problematic with respect to their transport across the blood-brain barrier, stability under physiological conditions, and selectivity towards neurofibrillary tangles and/or senile plaques.

Therefore, while various compositions and methods for imaging senile plaques and/or neurofibrillary tangles are known in the art, all or almost all of them suffer from one or more disadvantages. Thus, there is still a need to provide improved imaging agents for the detection of senile plaques and neurofibrillary tangles.

SUMMARY OF THE INVENTION

The present invention is directed to compositions and methods for labeling or treatment of neural diseases that are characterized by presence of senile plaques and neurofibrillary tangles. Most preferably, contemplated compounds are derivatives of FDDNP and curcumin and exhibit improved solubility in aqueous solvents. Preferred compounds further exhibit improved binding specificity and are labeled with a PET detectable label (e.g., $^{11}$C or $^{19}$F).

In one aspect of the inventive subject matter, a compound has a structure according to Formula I Formula I wherein Z is C(CN)$_2$ or O; wherein W is N—Y or CH$_2$, with the proviso that where W is N—Y then n is 1, and with the further proviso that where W is CH$_2$ then n is an integer between 0 and 2; Y is optionally substituted lower alkyl, optionally comprising a $^{11}$C atom; R$_1$ is hydrogen, lower alkyl, lower dialkylketone, or substituted aryl; wherein F is $^{18}$F or $^{19}$F; and wherein X is H or a radical that increases solubility of the compound in an aqueous solvent relative to the same compound in which X is H.

In certain embodiments it is generally preferred that Z is C(CN)$_2$, and that R$_1$ is hydrogen, lower alkyl, or lower dialkylketone. In such compounds, it is further preferred that F is $^{18}$F or $^{19}$F and that Y is CH$_3$, or that Y is $^{11}$CH$_3$ and F is $^{19}$F.

Further, it is preferred that in contemplated compounds X is H, OH, OCH$_3$, SH, NH$_2$, NHR$_2$, or NR$_2$R$_3$, wherein R$_2$ and R$_3$ are independently optionally substituted lower alkyl, and/or that R$_1$ is hydrogen or CH$_2$C(O)CH$_3$. Thus, especially preferred compounds will have a structure according to Formula II or IIa (where n is an integer between 0 and 4, and wherein X is OH, OR, SH, SR, NH2, NHR, C(O)R, C(O)OR, or optionally substituted R, wherein R is lower alkyl)

Formula II

Formula IIa

Alternatively, it is also contemplated that in compounds according to Formula I Z is O, and R$_1$ is substituted aryl. Most preferably, the substituted aryl in such compounds is selected from the group consisting of In yet another aspect of the inventive subject matter, contemplated compounds have a structure according to Formula III Formula III wherein R$_1$ and R$_4$ are independently H, OCH$_3$, OH, OX, lower Y-alkoxy, or lower $^{18}$F-alkoxy, wherein X is a protecting group for a hydroxyl group, and wherein Y is a leaving group; wherein R$_5$ is H, or where R$_4$ is not lower $^{18}$F-alkoxy then R$_5$ is lower $^{18}$F-alkyl; wherein R$_2$ and R$_3$ are independently H, or lower alkoxy, optionally comprising a $^{11}$C atom; Q is an optional protecting group for the diketone and covalently bound to the diketone group when Q is present. In such compounds it should be noted that the compound does not comprise the $^{11}$C atom when R$_5$ is lower $^{18}$F-alkyl or when R$_1$ or R$_4$ is lower $^{18}$F-alkoxy, and that the compound comprises one of the $^{11}$C atom, the lower $^{18}$F-alkyl, and the lower $^{18}$F-alkoxy.

In preferred compounds according to Formula III lower $^{18}$F-alkoxy is —O—(CH$_2$)$_3$$^{18}$F, and lower $^{18}$F-alkyl is —(CH$_2$)$_3$$^{18}$F. Additionally, it is preferred that R$_1$ and R$_4$ are OH, and/or R$_2$ and R$_3$ are OCH$_3$, and/or that R$_2$ is OCH$_3$ and R$_3$ is O$^{11}$CH$_3$. In certain preferred compounds, R$_2$ and R$_3$ are H, R$_1$ is OH, and R$_3$ is lower $^{18}$F-alkoxy. Particularly preferred compounds also include intermediates in which R$_1$ is OX, R$_4$ is lower Y-alkoxy, and in which Q is a boron-containing protecting group of the diketone.

In yet another aspect of the inventive subject matter, contemplated compounds have a structure according to Formula IIIa Formula IIIa wherein R is H, CH$_3$, lower alkyl, substituted phenyl, substituted benzyl, substituted styryl; X is OH, OCH$_3$, O-alkyl, O-fluoroalkyl, NH$_2$, NHR, optionally labeled with $^{11}$C— or $^{18}$F—; Y is OH, OCH$_3$, alkyl, fluoroalkyl, optionally labeled with $^{11}$C— or $^{18}$F—; and wherein the compound comprises at least one of $^{11}$C— and $^{18}$F.

In a still further aspect of the inventive subject matter, pharmaceutical and diagnostic compositions are contemplated in which the compounds according to the inventive subject matter are combined with a pharmaceutically acceptable carrier. Consequently, various methods of imaging or treating a neural disorder in a subject are also contemplated in which the pharmaceutical or diagnostic compositions are administered to a subject in need thereof.

Various objects, features, aspects and advantages of the present invention will become more apparent from the following detailed description of preferred embodiments of the invention.

DETAILED DESCRIPTION

The inventors have discovered various imaging agents that can be used to detect amyloid plaques and neurofibrillary tangles in the brain. Among other advantages, contemplated imaging agents exhibit relatively high specificity with respect to the labeling target and have significantly improved solubility in aqueous systems (and with that reduced non-specific binding to lipophilic non-target tissue and structures). Among other compounds, the inventors have synthesized $^{18}$F-FBM (4'-[(2-[$^{18}$F]fluoroethyl)(methyl)amino]-4-phenyl-3-buten-2-malonitrile) and $^{18}$F-FPCUR ($^{18}$F-fluoropropylcurcumin) and preformed in vitro studies on Tg2576 and triple transgenic mice brains. In these studies, compounds according to the inventive subject matter were less lipophilic and showed significant and specific binding to plaques in the hippocampus. Thus, and among various other uses, contemplated compounds and compositions can be employed for early diagnosis or even therapy of Alzheimer's and various other diseases associated with amyloid plaques and neurofibrillary tangles in the brain.

Based on the above considerations and other contemplations, the inventors used in one approach rationally guided alterations of FDDNP to render it less lipophilic, and therefore to increase its specific binding. In another approach, the inventors applied these alterations to the structure of curcumin, which is a natural product known to bind to plaques to achieve more accurate detection of plaques and tangles in the brain. For example, to reduce the lipophilicity of FDDNP, FBM and derivatives were designed which contained two less carbon atoms as compared to FDDNP. Such new compounds could be easily radiolabeled for further use in vitro or in vivo. For example, several of contemplated compounds were tested for binding on wild-type mice, transgenic Tg 2576 mice, and triple transgenic mice brain slices (Tg 2576 mice are known to be a good model of Alzheimer's disease characterized by plaque accumulation; triple transgenic mice are known to express both plaques and tangles in an age dependent manner). In another example, to maintain properties of curcumin to bind to plaques, various analogs of curcumin were developed and labeled (e.g., $^{18}$F-fluoropropylated on a phenolic OH group). The structures below depict the known compound $^{18}$F-FDDNP, and representative compounds of the structures presented herein As is apparent from the above structures and experimental data provided below, $^{18}$F-FBM is less lipophilic than $^{18}$F-FDDNP, while still having structural similarities to $^{18}$F-FDDNP. Still further, $^{18}$F-FBM is also able to provide higher target to non-target ratios than $^{18}$F-FDDNP in the transgenic mice hippocampus. The Tg2576 and triple transgenic mice brains have been shown to be a good model for Alzheimer's disease, because of the similar accumulation of beta-amyloid plaques. $^{18}$F-FBM also unexpectedly showed specific binding in the frontal cortex of the transgenic mouse brain. Further evaluation of FBM in other brain regions and in vitro binding affinity studies of FBM to the β-amyloid binding sites may therefore also enable research to better understand how $^{18}$F-FBM binds to plaques all over the brain.

In one preferred aspect of the inventive subject matter, compounds are contemplated in which FDDNP served as a template for modifications that would improve solubility and/or specificity of the binding agent, and particularly preferred compounds have a structure according to Formula I Formula I in which Z is C(CN)$_2$, S, NR$_1$, or O; wherein W is N—Y or CH$_2$, with the proviso that where W is N—Y then n is 1, and with the further proviso that where W is CH$_2$ then n is an integer between 0 and 2; Y is optionally substituted lower alkyl, optionally comprising a $^{11}$C atom; R$_1$ is hydrogen, optionally substituted lower alkyl, optionally substituted lower dialkylketone, or substituted aryl; wherein F is $^{18}$F or $^{19}$F; and wherein X is H or a radical that increases solubility of the compound in an aqueous solvent relative to the same compound in which X is H.

In certain embodiments it is generally preferred that Z is C(CN)$_2$, and that R$_1$ is hydrogen, lower alkyl, or lower dialkylketone. In such compounds, it is further preferred that F is $^{18}$F or $^{19}$F and that Y is CH$_3$, or that Y is $^{11}$CH$_3$ and F is $^{19}$F. Further, it is preferred that in contemplated compounds X is H, OH, OCH$_3$, SH, NH$_2$, NHR$_2$, or NR$_2$R$_3$, wherein R$_2$ and R$_3$ are independently optionally substituted lower alkyl, fluoroalkyl and/or that R$_1$ is hydrogen or CH$_2$C(O)CH$_3$. Thus, especially preferred compounds will have a structure according to Formula IA, Formula IB, and Formula II

Formula IA

Formula IB

Formula II

Furthermore, it is contemplated that in compounds according to Formula I when Z is O, R$_1$ is substituted aryl or heterocycle. Most preferably, the substituted aryl in such compounds is selected from the group consisting of Additionally, compounds according to Formula IIa are also contemplated in which n is an integer between 0 and 4, and wherein X is OH, OR, SH, SR, NH2, NHR, C(O)R, C(O)OR, or optionally substituted R, wherein R is lower alkyl Formula IIa

In another preferred aspect of the inventive subject matter, contemplated compounds have a structure according to Formula III Formula III wherein R$_1$ and R$_4$ are independently H, OCH$_3$, OH, OX, lower Y-alkoxy, or lower $^{18}$F-alkoxy (all of which may be independently substituted), wherein X is a protecting group for a hydroxyl group, and wherein Y is a leaving group; wherein R$_5$ is H, or where R$_4$ is not lower $^{18}$F-alkoxy then R$_5$ is lower $^{18}$F-alkyl; wherein R$_2$ and R$_3$ are independently H, or lower alkoxy, optionally comprising a $^{11}$C atom (all of which may be independently substituted); Q is an optional protecting group for the diketone and covalently bound to the diketone group when Q is present. In such compounds it should be noted that the compound does not comprise the $^{11}$C atom when R$_5$ is lower $^{18}$F-alkyl or when R$_1$ or R$_4$ is lower $^{18}$F-alkoxy, and that the compound comprises preferably only one of the $^{11}$C atom, the lower $^{18}$F-alkyl, and the lower $^{18}$F-alkoxy. However, multiple labeling is not excluded from contemplated compounds.

In preferred compounds according to Formula III lower $^{18}$F-alkoxy is —O—(CH$_2$)$_3$$^{18}$F, and lower $^{18}$F-alkyl is —(CH$_2$)$_3$$^{18}$F. Additionally, it is preferred that R$_1$ and R$_4$ are OH, and/or R$_2$ and R$_3$ are OCH$_3$, and/or that R$_2$ is OCH$_3$ and R$_3$ is O$^{11}$CH$_3$. In certain preferred compounds, R$_2$ and R$_3$ are H, R$_1$ is OH, and R$_3$ is lower $^{18}$F-alkoxy. Particularly preferred compounds also include intermediates in which R$_1$ is OX, R$_4$ is lower Y-alkoxy, and in which Q is a boron-containing protecting group of the diketone.

Still further contemplated compounds are those according to Formula IIIa in which R is H, CH$_3$, lower alkyl, substituted phenyl, substituted benzyl, substituted styryl, X is OH, OCH$_3$, O-alkyl, O-fluoroalkyl, NH$_2$, NHR, optionally labeled with $^{11}$C— or $^{11}$F—, Y is OH, OCH3, alkyl, fluoroalkyl, optionally labeled with $^{11}$C— or $^{18}$F—, and wherein the compound comprises at least one of $^{11}$C— and $^{18}$F.

Formula IIIa

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.). As still further used herein, the term "alkoxy" refers to a —OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or optionally substituted cycloheteroalkyl.

Furthermore, the term "aryl" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Similarly, the terms "heterocycle" or "heterocyclic ring" are used interchangeably herein and refer to a saturated, partially or entirely unsaturated, or aromatic carbocyclic group having a single ring (e.g., morpholino, pyridyl or furyl) or multiple condensed rings (e.g., naphthpyridyl, quinoxalyl, quinolinyl, or indolizinyl) which include at least one heteroatom within the ring(s). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthio, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

It should further be recognized that the compounds contemplated herein may also be active and/or prepared as a metabolites, as prodrugs, and/or otherwise modified compound, wherein the metabolite, prodrug, or modified compound exhibits higher permeability across the blood brain barrier or less toxicity as compared to the unmodified compound and wherein the prodrug or modified compound is converted within the target cell/organ/structure back into the unmodified form. For example, conversion of contemplated compounds into prodrugs may be useful where the active drug is too toxic for safe systemic administration, or where the contemplated compound is less rapidly transported across the blood brain barrier, or where the body breaks down the compound before reaching its target. Contemplated compounds may also be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc. Similarly, contemplated compounds may be formulated such as to facilitate transport across the blood brain barrier, and all known formulations are deemed suitable for use herein.

Based on the observed and/or expected improved solubility and specificity of compounds contemplated herein, it should be recognized that these compounds may be employed for various pharmaceutical, diagnostic, and research uses. Among other uses, it is contemplated that the compounds will allow early diagnosis of formation of senile plaques and/or neurofibrillary tangles, and will allow to more precisely locate and even quantify such plaques and tangles. In still further contemplated aspects, it is also thought that the compounds presented herein may be employed to reduce or even prevent formation of senile plaques and/or neurofibrillary tangles. Thus, it is contemplated that the compounds and compositions according to the inventive subject matter are suitable for diagnostic and/or therapeutic (including prophylactic) purposes.

Consequently, a pharmaceutical composition may include at least one of contemplated compounds (preferably in oral or parenteral formulation) at a concentration effective to treat a disease associated with development of presence of senile plaques and/or neurofibrillary tangles. Compounds in such compositions will typically not be labeled. On the other hand, compounds in diagnostic compositions will preferably be labeled with a PET detectable label (e.g., $^{11}$C or $^{18}$F) at a specific activity that allows in vivo acquisition of a signal. Consequently, pharmaceutical or diagnostic compositions comprising compounds presented herein are especially contemplated. Similarly, methods of imaging or treating (including prophylactic treatment) a neural disorder in a subject are contemplated in which compositions comprising compounds presented herein are administrated at a dosage effective to image or treat the disorder. For example, contemplated methods of diagnosing a mammal having a disease or condition that is associated with senile plaques and neurofibrillary tangles includes a step in which contemplated compounds are administered to the mammal (typically in a labeled form) at a dosage effective to locate and/or quantify in vivo binding of the labeled compound to the senile plaques and/or neurofibrillary tangles. Preferably, the label is an isotope suitable for detecting the compound in vivo using PET (most preferably $^{18}$F), and contemplated compounds are parenterally administered. Viewed from a different perspective, compositions comprising contemplated compounds will be useful in the treatment, prevention, diagnosis and/or therapeutic follow-up of Alzheimer's disease, minimal cognitive impairment, dementia, inflammation associated with these neurological processes, inflammation as a result of other injuries, or pathophysiologies related to cancer.

Particularly preferred compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intrathecal, intralesional, and intracranial administration (typically injection or infusion). Preferably, the compositions are administered orally, intraperitoneally, or intravenously. Such compositions are prepared according to techniques well-known in the art of pharmaceutical formulation and may be prepared as solutions in saline, employing benzyl alcohol or other suitable preservatives, absorption promoters to enhance bioavailability and/or transport across the blood-brain barrier, fluorocarbons, and/or other conventional solubilizing or dispersing agents.

With respect to the amount of contemplated compounds in the composition, it should be recognized that the particular quantity will typically depend on the specific formulation, particular compound, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in a liquid carrier (single solvent or complex solvent system, preferably monophasic) in amount of between about 0.1 μg/ml to about 500 mg/ml, more typically in an amount of between about 10 μg/ml to about 100 mg/ml, and most typically between about 1 μg/ml to about 10 mg/ml. Where the formulation is a solid, contemplated compounds will be present in an amount of between about 0.1 μg/g to about 900 mg/g, more typically in an amount of between about 10 μg/g to about 500 mg/g, and most typically between about 1 mg/g to about 200 μg/g. With respect to a dosage unit, it is generally contemplated that contemplated compounds are administered at a dosage effective to achieve a desired therapeutic effect or at a dosage effective to provide visualization in vitro and/or in vivo. Therefore, suitable amounts of contemplated compounds will be in the range of 0.1 μg per dosage unit to about 0.5 gram per dosage unit, more typically between 10 μg per dosage unit to about 0.05 gram per dosage unit, and most typically between 50 μg per dosage unit to about 100 mg per dosage unit. Thus, suitable dosages will be in the range of about 0.1 μg/kg and 10 mg/kg, more typically between 1 μg/kg and 5 mg/kg, and most typically between 10 μg/kg and 1 mg/kg.

With respect to suitable labeling amounts, it is generally contemplated that all quantities are deemed suitable that can be detected using an in vitro and/or in vivo imaging technology, and particularly in vivo PET. Typically, a radiolabeling precursor compound will be labeled with a fluorine-18 source by an imaging center. For example, several microcuries to several millicuries will be produced and then used for imaging studies. Therefore, contemplated compounds and kits may also include at least one of a precursor molecule, the labeling molecule containing $^{18}F$, and the $^{18}F$ labeled ligand.

Experiments

To evaluate differences in molecular structure of FDDNP and its derivatives having less carbon atoms (and with that less lipophilic character), computer modeling was employed for various compounds. For example, 3-D Chemdraw and Alchemy software packages were used to model the FDDNP and FBM. When the chemical structures of $^{18}F$-FDDNP and $^{18}F$-FBM were evaluated with 3-D Chemdraw the two energy minimized structures indicated a very similar backbone structure, suggesting that FBM is likely to bind to the same site as FDDNP. The energy minimized chemical models of $^{18}F$-FDDNP (Model A) and $^{18}F$-FBM (Model B) shown below exhibit highly similar backbone structure.

Synthesis of Selected Compounds

Unless indicated otherwise, all chemicals and solvents were obtained from Aldrich Chemical Co. Electrospray mass spectra was obtained on a Model 7250 mass spectrometer (Micromass LCT), and proton magnetic resonance spectra ($^1H$-NMR) were acquired on a GE NMR Omega 500-MHz spectrometer. Reactions were monitored by carrying out thin-layer chromatography (TLC).

It should be noted that the synthesis methods of FBM varied from the ones employed for FDDNP, to accommodate for their difference in structure, and one exemplary scheme for the synthesis of $^{18}F$-FBM is depicted in Scheme 1 below.

<sup>18</sup>F-FBM

Synthesis of FBM started by reacting N-methyl-N-(2-hydroxyethyl)-4-aminobenz-aldehyde (1 g, 5.59 mmol) dissolved in 4 mL of ethanol with excess acetone (4 mL) in aqueous sodium hydroxide solution (0.4 g in 4 mL water) following a reported procedure (Masuda T, et al. (1993). Anti-oxidative and Anti-inflammatory Curcumin-Related Phenolics From Rhizomes of Curcuma Domestica. Phytochemistry 32(6), 1557-1560). The reaction was stirred at room temperature for a little over an hour. The mixture was purified and separated by preparative TLC, silica to provide the benzylidene acetone derivative in approx. 16% yield (200 mg). This acetone derivative, 4'-[(2-hydroxyethyl)(methyl) amino]-4-phenyl-3-buten-2-one (50 mg, 0.23 mmol), was then reacted with malononitrile (15 mg, 0.23 mmol) in pyridine (1.7 mL) at 95° C. for 24 hours. The solvent was removed in vacuo, and the residue was chromatographed by preparative TLC to obtain the malonitrile derivative, 4'-[(2-hydroxyethyl)(methyl)amino]-4-phenyl-3-buten-2-malonitrile in approx 40% yield (24 mg). In order to prepare FBM, the tosylate precursor, 4'-[(2-tosyloxyethyl)(methyl)amino]-4-phenyl-3-buten-2-malonitrile was prepared by reacting 4'-[(2-hydroxyethyl)(methyl)amino]-4-phenyl-3-buten-2-malonitrile (20 mg, 0.07 mmol) with on equivalent of p-toluenesulfonyl chloride and pyridine (8 µL) in dichloromethane initially at ice-bath temperature and stirred at room temperature for 24 hours. Pyridine and dichloromethane were removed under vacuum and the residue was chromatographed using preparative TLC to give the tosylate precursor, 4'-[(2-tosyloxyethyl)(methyl)amino]-4-phenyl-3-buten-2-malonitrile in approx. 20% yield (6 mg). Finally, the tosylate precursor was treated with tetrabutylammonium fluoride to provide the reference compound, FBM.

Of course, it should be appreciated that by the choice of a particular starting material and specific reagents, numerous modifications of FBM can be obtained. For example, N-methyl-N-(2-hydroxyethyl)-4-aminobenz-aldehyde may be substituted to include one or more substituents on the phenyl group and/or the nitrogen atom. Among other things, the benzaldehyde group may comprise a halogen or leaving group on the phenyl ring, and/or the substituents on the nitrogen may be changed to a hydroxyalkyl or hydroxylaryl group (of course, the hydroxyl group may also be replaced by a non-hydroxy group. In another example, a 2-n-hydroxyalkyl-4-benzaldehyde (with n between 2 and 5 and alkyl between ethyl and pentyl) could be employed to yield a hydroxyalkyl side chain in a final product.

In still further examples, the dimethylketone reagent may be replaced with numerous alternative reagents, including various optionally substituted dialkylketones, dialkylthioketones, and dialkylamines to obtain the corresponding keto, thioketo, or imino group. Similarly, the malonitrile reagent could be replaced by various other substituted malic acid or other derivatives to obtain different substitution patterns on the side chain.

For the radiosynthesis step, high specific activity $^{18}$F-fluoride (approximately 100 milliCurie) was produced in the MC-17 cyclotron. Fluorine-18 radioactivity count was measured in a Capintec dose calibrator, while low-level counts were measured out in a well-counter (Cobra Quantum, Packard Instruments Co). Direct radiolabeling of the tosylate precursor was done by using $^{18}$F-fluoride in a solution of 19 mg of Kryptofix 2.2.2 and 0.75 mg potassium carbonate in acetonitrile. The mixture was heated at 85° C. for 20 minutes. After cooling, the mixture was transferred onto a neutral alumina Sep-Pak Cartridge to remove unreacted $^{18}$F-fluoride. Chromatographic separations were preformed on semi-preparative reverse-phase C18 column (length=250 nm, ID=4.6 mm) using the Gilson high performance liquid chromatography (HPLC) systems. Decay-corrected radiochemical yield was approx. 20%. Retention time of $^{18}$F-FBM was 14 mins compared to 15.7 mins for $^{18}$F-FDDNP (for separation protocol, see e.g., Agdeppa E D et al. (2001) Binding Characteristics of Radiofluorinated 6-Dialkylamino-2-Naphthylethylidene Derivatives as Positron Emission Tomography Imaging Probes for Beta-Amyloid Plaques in Alzheimer's Disease. *The Journal of Neuroscience* 21, 1-5). $^{18}$F-FBM was collected and prepared for in vitro binding studies. Specific activities of >2000 Ci/mmol were obtained for both $^{18}$F-FBM and $^{18}$F-FDDNP, using RP-HPLC (CH3CN:H2O 0.1% Et3N, 58%:42%; flow rate 2.5 ml/min).

It should be noted that an initial reaction of 2-methylaminoethanol (1.5 mL) with 4-hydroxybenzylideneacetone (0.68 g) in NaHSO$_3$ (0.78 g) and H$_2$O (1.5 mL) in a sealed vial at 140° C. for 16 hrs did not provide the necessary benzylidene acetone derivative (Scheme 1, compound (b)). Therefore, N-methyl-N-(2-hydroxyethyl)-4-aminobenzaldehyde (Scheme 1, compound (a)) was purchased and used to complete the first step of synthesis instead. When the benzylidene acetone derivative was spotted on a TLC plate the compound glowed fluorescently. The benzylidene acetone derivative reaction mixture was spotted onto preparative TLC plate for purification. Three distinct bands can be observed: a red band at the bottom of the plate, yellow band at the middle, and a faint band at the top were observed. Using mass spectra the inventors determined that the middle yellow band contained the actual benzylidene acetone derivative.

After filtering out the silica and using ethyl acetate to purify the compound, the inventors found that the reaction provided a relatively low yield of 17.9% of the benzylidene acetone derivative (Scheme 1, compound (b)). For the second step of synthesis, the malonitrile derivative (Scheme 1, compound (c)) was prepared using procedures similar to that reported for FDDNP (Agdeppa et al., see above). The reaction mixture was spotted on TLC plate and displayed many colorful spots, demonstrating that the mixture was not very pure. Purification of the reaction mixture was carried out on preparative TLC plate to provide pure malonitrile derivative (Scheme 1, compound (c)). Successful tosylation of the malonitrile derivative was carried out by using p-toluenesulfonyl chloride. However, the yield of the reaction was found to be relatively low to provide the desired tosylate (Scheme 1, compound (d)).

Radiolabeling

Radiolabeling of the tosylate (Scheme 1, compound (d)) proceeded smoothly in the automated radiosynthesis unit giving a good 30-40% radiochemical yield of $^{18}$F-FBM. These radiochemical yields of $^{18}$F-FBM were similar to $^{18}$F-FDDNP yields obtained (30-40%). Purification of the product was carried out using a reverse-phase HPLC system which is better than the reported purification of $^{18}$F-FDDNP using a normal phase. Retention time of $^{18}$F-FBM was 14 mins compared to 15.7 mins for $^{18}$F-FDDNP. HPLC showed that $^{18}$F-FBM in fact comes out first, indicating that $^{18}$F-FBM is less lipophilic than $^{18}$F-FDDNP.

Binding Analysis of $^{18}$F-FBM

In vitro studies of $^{18}$F-FBM were carried out on coronal and horizontal mice brain slices (both wild-type and Tg 2576), which were obtained on a Leica 1850 cryotome. Mice brain-region slices (hippocampus and frontal cortex of 24-month old wild-type and Tg 2576; 10 μm thick) were preincubated in buffer (0.9% saline) for 10 minutes. Subsequently, the mice brain slices were incubated with $^{18}$F-FBM (6.8 μCi/cc) in 0.9% saline, pH 7.4 at 37° C. for 1 hr. For nonspecific binding, brain slices were treated with 10 μM FDDNP. Slices were washed with cold millipore water, 70% alcohol, 90%, alcohol, 70% alcohol, and water for 2, 1, 1, 1, and 1 min, respectively. The slices were air dried then exposed overnight onto a phosphor screen and read by the Phosphor Autoradiographic Imaging System/Cyclone Storage Phosphor System (Packard Instruments Co). Regions of interest were drawn on various regions of the slices and the extent of binding of $^{18}$F-FBM was computed as DLU/mm$^2$ using the OptiQuant acquisition and analysis program (Packard Instruments Co).

Similar experiments were carried out in adjacent slices using $^{18}$F-FDDNP (7.8 μCi/cc) for comparison. For evaluating the amount of plaque present in the brain slices, adjacent brain slices were also stained for the peptide fragment Aβ17-24 which is representative of the amount of Aβ40 and Aβ42 plaque aggregates using reported 4G8 immunostaining methods of UCI-Institute for Brain Aging and Dementia (Head E, Moffat K, Das P, Sarsoza E, Poon W W, Landsberg G, Cotman C W, Muphy M P. (2005). Beta-amyloid deposition and tau phosphorylation in clinically characterized aged cats. *Neurobiology of Aging* 26(5): 749-763). Beta-amyloid deposition and tau phosphorylation in clinically characterized aged cats. *Neurobiology of Aging* 26(5): 749-763).

In Vitro Analysis in Tg2576 Mice

Figure 1:
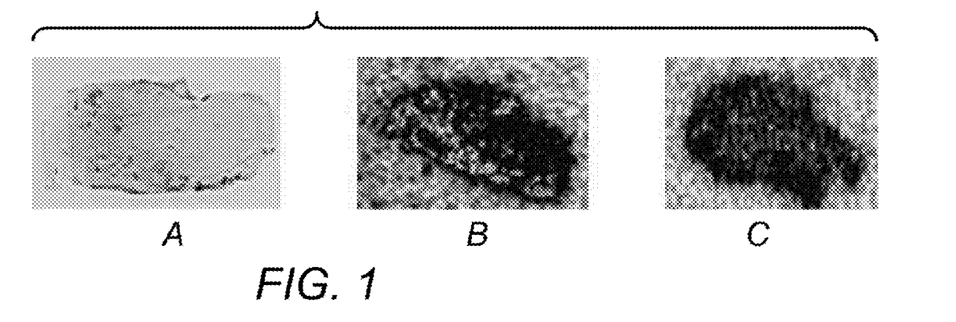
FIGS. 1A-1C are photomicrographs of hippocampal brain slices of transgenic mice stained with antibodies specific towards β-amyloid plaques (A), radiolabeled with $^{18}$F-FBM in the absence of competing FDDNP (B), and radiolabeled with $^{18}$F-FBM in the presence of competing FDDNP (C).
Figure 2:
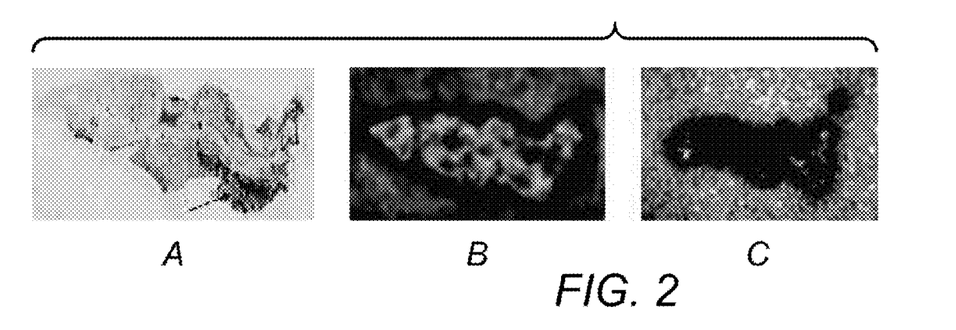
FIGS. 2A-2C are photomicrographs of hippocampal brain slices of transgenic mice stained with antibodies specific towards β-amyloid plaques (A), radiolabeled with $^{18}$F-FDDNP in the absence of competing FDDNP (B), and radiolabeled with $^{18}$F-FBM in the presence of competing FDDNP (C).

Hippocampal slice of 24-month old transgenic mouse (Tg2576, transgenic mice expressing mutant APP) stained for Aβ17-24 using 4G8 immunostaining confirmed presence of β-amyloid plaques found in Alzheimer's disease (FIGS. 1A and 2A depicting 10 μm thick horizontal hippocampal slice of 24-month old transgenic mouse (Tg2576) stained for Aβ17-24 using 4G8 immunostaining. Arrow indicates amyloid plaques.). Adjacent hippocampal slices radiolabeled with $^{18}$F-FBM and $^{18}$F-FDDNP indicated binding to amyloid plaques and corresponded to the 4G8 stain (FIGS. 1B and 2B depicting adjacent hippocampal slice shown in (A) but radiolabeled with high-specific activity $^{18}$F-FBM or $^{18}$F-FDDNP. Arrow indicates binding of $^{18}$F-FBM or $^{18}$F-FDDNP to the amyloid plaques and corresponds to the 4G8 stain.). The specific binding to amyloid plaques was reduced in the presence of 10 μM FDDNP (FIGS. 1C and 2C; FIG. 1C depicts adjacent hippocampal slice shown in (B) radiolabeled with high-specific activity $^{18}$F-FBM in the presence of 10 μM FDDNP. Specific binding to regions containing plaques is reduced; and FIG. 2C depicts adjacent hippocampal slice in cold FDDNP. Specific binding to plaque regions is reduced). Alcohol was used for washing the medium to remove nonspecific binding. The ratio of binding in plaque to non-plaque areas within the same slice for $^{18}$F-FBM was 2.1 while that for $^{18}$F-FDDNP was 1.4; and in the presence of 10 μM FDDNP, these ratios went down to 1.6 and 1.2, respectively. Thus, $^{18}$F-FBM showed higher specific binding to amyloid plaque regions compared to $^{18}$F-FDDNP.

In Vitro Analysis in Triple Transgenic Mice

Figure 3:
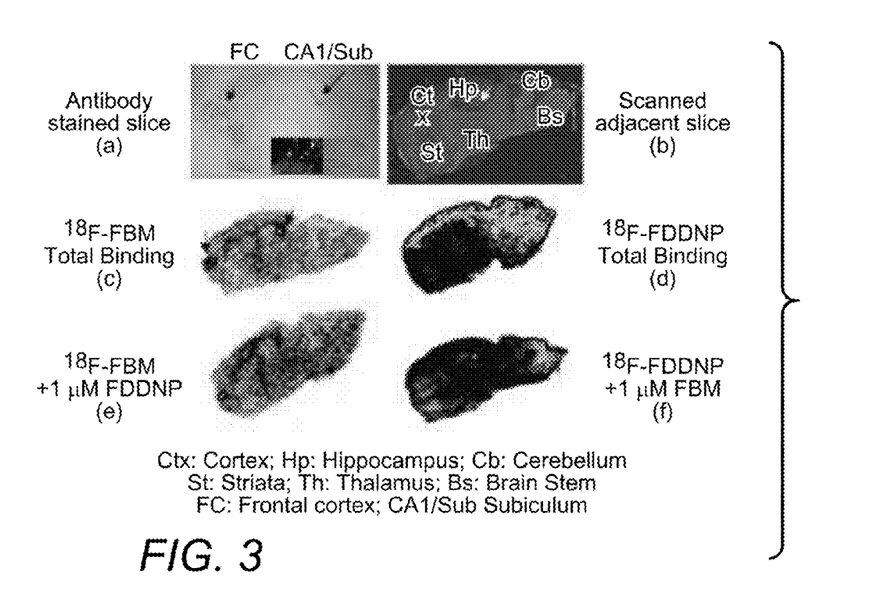
FIG. 3 shows selected results of binding studies in 10 micron thick brain slices of a triple transgenic mouse brain with antibodies for plaques (A), $^{18}$F-FBM (B, C) and comparison with $^{18}$F-FDDNP (D, E, F).

Sagittal brain slices of 18 month old triple transgenic mice were then studied. These mice have been known to have an extensive amount of senile plaques and neurofibrillary tangles accumulation in several regions of the brain. These regions include the hippocampus, cortex, thalamus, brain stem and other regions. Binding of $^{18}$F-FBM and $^{18}$F-FDDNP to 10 micron thick slices of triple transgenic mice brains is depicted in FIG. 3 along with antibody staining for plaques. More specifically, FIG. 3A depicts antibody staining in the hippocampus and frontal cortex regions, which was also confirmed by thioflavin S staining in an adjacent slice (shown in inset in FIG. 3A). FIG. 3B shows the various brain regions in the section which are of interest in the binding of $^{18}$F-FBM. The selective binding of $^{18}$F-FBM to the regions that have a high concentration of the plaques is seen in FIG. 3C. Regions of the hippocampus and the frontal cortex (arrows pointing) that contain the plaques are clearly evident. This selective binding is significantly reduced in the presence of high concentrations (1 μM) FDDNP as seen in FIG. 3E. Binding of $^{18}$F-FDDNP is demonstrated in the hippocampus and other regions in FIG. 3D. However, a significant amount of binding is also seen in the cerebellum which does not contain significant amount of plaques. Thus, it should be appreciated that $^{18}$F-FDDNP is less selective for binding to the plaques. In the presence of high concentration of FBM (1 mM) binding of $^{18}$F-FDDNP was reduced in the hippocampus, as can be seen in FIG. 3F.

Figure 4A:
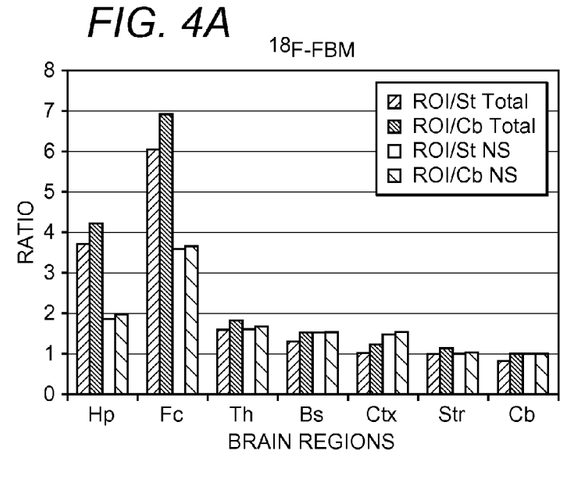
FIGS. 4A and 4B depict graphs showing binding of $^{18}$F-FBM (A) and $^{18}$F-FDDNP (B) in various plaque containing regions of murine brain.
Figure 4B:
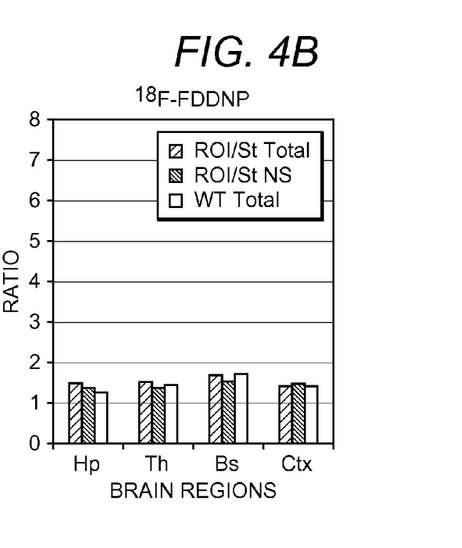

The binding of $^{18}$F-FBM in the various plaque containing regions was also quantitatively evaluated as a ratio plot shown in FIGS. 4A and 4B. Cerebellum and striatum were used as reference regions. Normally cerebellum would be used, but since cerebellum was found to be unsuitable for $^{18}$F-FDDNP while striatum seemed more optimal the inventors have used both regions for $^{18}$F-FBM. The ratio between the frontal cortex regions showing plaques was between 6 and 7 while the hippocampus was between 3.5 and 4.5 as can be taken from FIG. 4A. These are remarkably high ratios, whereas other regions showed modest binding. On the other hand, in the case of $^{18}$F-FDDNP, the binding ratios with respect to cerebellum were 1.5 and 2.0 as can be taken from FIG. 4B.

This clearly suggests that $^{18}$F-FBM is more suitable as an imaging agent than $^{18}$F-FDDNP for the study of Alzheimer's disease.

Curcumin

Curcumin, one of the active ingredients of turmeric has recently been shown to have unique physiological properties, including anti-inflammatory, anti-carcinogenic, and other activities. More recently, it has been shown to be of significant value in reducing the formation of amyloid plaques. Curcumin traverses into the brain readily and has little side effects. The inventors have now successfully radiolabeled curcumin with a $^{18}$F-fluoropropyl group (and other labeling moieties, not shown), which will allow study of biodistribution and pharmacokinetics of curcumin in the brain as well as provide further insights into the development of imaging agents for amyloid plaques. Curcumin is known to form complexes with metal ions due to its unique diketone structure (see FIG. 5) which readily enolizes. The inventors expected three potential sites where curcumin could be $^{18}$F-fluoropropylated: the phenolic group in either rings, the oxygen of the enolate and the carbon of the enolate.

1-Bromo-3-$^{18}$F-fluoropropane

1-Bromo-3-$^{18}$F-fluoropropane was prepared by reacting 1,3-dibromopropane with high specific activity $^{18}$F-fluoride at 90° C. in acetonitrile for 20 mins. Curcumin (from Sigma; cucuminoid content >94%) was then reacted with 1-bromo-3-$^{18}$F-fluoropropane in THF in the presence of sodium methoxide at 90-100° C. for 20 mins as further shown below.

$^{18}$F-fluoropropylcurcumin

Figure 5:
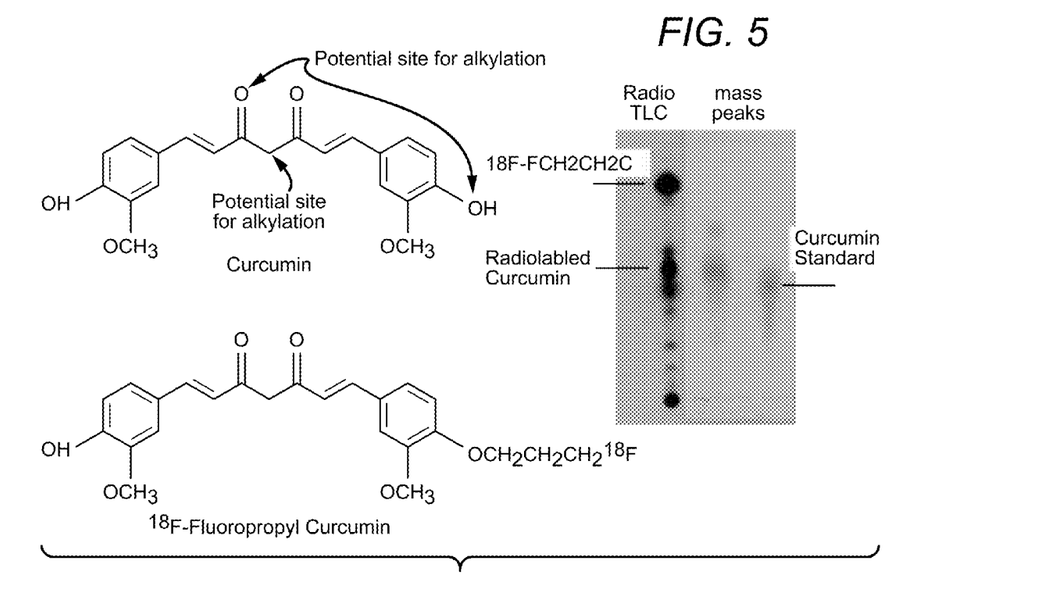
FIG. 5 schematically depicts various alkylation sites in curcumin and curcumin analogs and corresponding radio-TLC tracks.

Addition of sodium methoxide to curcumin generated a small red precipitate in THF into which the 1-bromo-$^{18}$F-fluoropropane solution was added. After the reaction, approx. 10% of the initial radioactivity remained. This reaction mixture was then taken in the HPLC buffer and purified by HPLC. Radiolabeling of curcumin occurred in low yields, only approximately 2-3% of the radioactivity corresponded to curcuminoid radiolabeling computed from collected HPLC fractions. Reaction mixture was purified on reverse phase HPLC (C-18 column, $CH_3CN$, $CH_3OH$, $H_2O$, $CH_3CO_2H$ 41:23:36:1; flow rate 1.5 ml/min). The product mixture was also evaluated by radio-TLC using 1:1 hexane-ethyl acetate. Radiolabeling and isolation of 1-bromo-$^{18}$F-fluoropropane as a THF solution occurred in >40% radiochemical yield in 50 mins. Radio-TLC also confirmed curcuminoid radiolabeling as shown in FIG. 5 and further characterization of the product mixture showed the formation of $^{18}$F-fluoropropyl-curcumin which is suitable for imaging studies of the transgenic mice models. Lane-1 in FIG. 5 shows fluorine-18 activity, lane-2 shows corresponding mass peaks and lane-3 shows pure curcumin. The cluster of radioactive spots corresponding to curcumin reflects $^{18}$F-fluoropropyl curcuminoids. Radiosynthesis of $^{18}$F-fluoropropylcurcumin ($^{18}$F-FPCUR) was accomplished in 5-10% radiochemical yield. Specific activities of ~1000 Ci/mmol were obtained for $^{18}$F-FPCUR using HPLC.

One exemplary synthetic approach for $^{18}$F-FPCUR is depicted in Scheme 2 below that also reflects improvements in the radiosynthesis of $^{18}$F-fluoropropylcurcumin ($^{18}$F-FPCUR). Here, synthesis of a curcumin-boron oxide complex (curcumin-B2O3) protected the diketone functionalities. Boron oxide (0.7 mg) and curcumin (3.7 mg) were heated in dimethylformamide (0.2 ml) at 80° C. for 30 mins to form the complex. This curcumin-boron oxide protecting group was used in order to protect the diketone in the compound, and prevent complex mixtures from forming. The $^{18}$F-1,3-bromofluoropropane (prepared as described previously) was then reacted with the curcumin-B2O3 complex in dimethylformamide along with potassium carbonate at 90° C. for 30 minutes to label the OH group on the complex. Subsequent to alkylation, 1 N HCl (0.2 ml) was added to deprotect the borate complex at 90° C. for 5 minutes. The radiochemical yield of this coupling step was approx. 5-10%, with a specific activity of about 1 Ci/mmol.

Of course, it should be appreciated that the particular choice of the curcumin starting material and isolation procedure will determined the final product. There are numerous natural and synthetic curcuminoid structures known in the art (e.g., bisdemethoxycurcumin, demethoxycurcumin, feruloyl-p-hydroxycinnamoylmethane, bis-(p-hydroxycinnamoyl)methane etc.), and all of them are deemed suitable for use herein.

Scheme 2

Curcumin-$B_2O_3$ Complex

-continued

18F-Fluoropropyl Curcumin
(18F-FPCUR)

Purification of $^{18}$F-FPCUR

Figure 6:
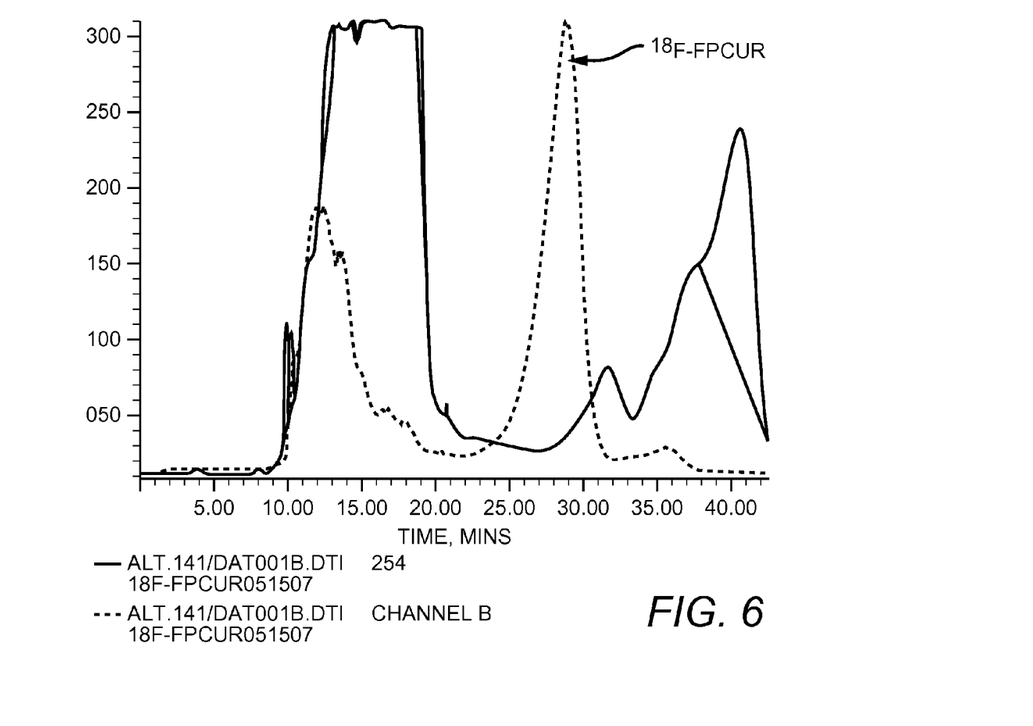
FIG. 6 depicts an HPLC elution profile in the purification of $^{18}$F-FPCUR.

Reverse phase HPLC was carried out for purification using C-18 Column, eluted with 55% acetonitrile, 45% of 1% citric acid, and at a flow rate of 1.5 ml/min. FIG. 6 shows the separation profile. $^{18}$F-FPCUR eluted at 28 mins and was separated from unreacted curcumin. Apparent specific activity was approx. 1000 Ci/mmol.

In Vitro Analysis of $^{18}$F-FPCUR in Transgenic Mice

Figure 7:
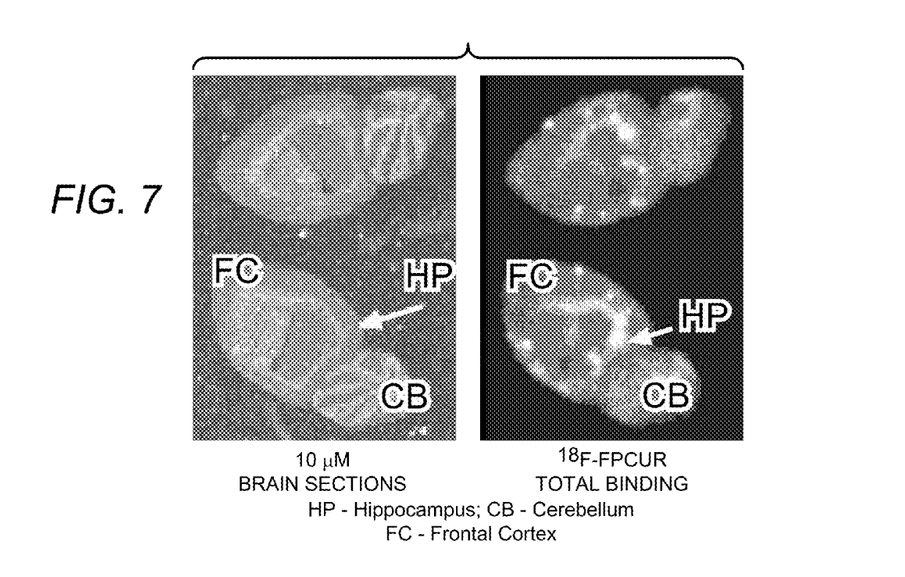
FIG. 7 depicts binding of $^{18}$F-FPCUR to the hippocampus (HP), regions of the frontal cortex (FC), and the cerebellum (CB).

Preliminary binding to rat brain slices of $^{18}$F-fluoropropyl curcumin was carried out at 37° C. in Tris buffer, 50 mM, pH 7.4 for one hour, and further testing of $^{18}$F-FPCUR for binding to β-amyloid plaques was carried out transgenic mice brains. 10 μm thick transgenic mice sagittal brain sections were cut (Tg 2576 and 3×Tg; 1 to 24 mo and comparable wild-types). Brain slices were pre-incubated for 10 mins in incubation buffer, 0.1 M Tris, 0.1 M NaCl, 0.5% Tween and 0.1% BSA, pH 7.4. Incubation was carried out in 0.1 M Tris, 0.1 M NaCl, 0.5% Tween and 0.1% BSA, pH 7.4 with $^{18}$F-FPCUR (3 μCi/cc) at 37° C. for 1 hr. For nonspecific binding, brain slices were treated with 10 μM CUR or 10 μM PIB. Slices were washed with cold buffer, 2×2 min, rinsed with cold water and air dried. Autoradiograms were obtained of various slices and binding of $^{18}$F-FPCUR was quantitated using Optiquant Image analysis program. FIG. 7 depicts binding of $^{18}$F-FPCUR to hippocampus (HP) and regions of the frontal cortex (FC), while little binding is seen in the cerebellum (CB). For evaluating the amount of plaque present in the brain slices, adjacent brain slices were also stained using reported immunostaining methods.

Therefore, it should be appreciated that selective binding of $^{18}$F-FPCUR can be achieved in transgenic mice expressing plaques (2576) in areas corresponding to those staining positive for the Aβ-42 immunostain. Hippocampus to cerebellum ratio was approx. 3.5 to 4. $^{18}$F-FPCUR was displaced by both PIB and Curcumin, both of which are known to bind to amyloid plaques. Selective binding of $^{18}$F-FPCUR was observed in transgenic mice expressing plaques and tangles. Increased binding of $^{18}$F-FPCUR was observed in older transgenic mice. A carbon-11 labeled analog of curcumin, as an analog of $^{18}$F-FPCUR which will be suitable for shorter duration studies.

Further contemplations, experimental details, and observations are provided in Mukherjee, J., Head, E., Pichika, R., Easwaramoorthy, B., Collins, D., Chen, I., Wang, C. S., Saigal, N., Trinidad, P., Kim, K. and Nguyen, V. L.: Radiotracers for a multi-target approach to the diagnosis of Alzheimer's disease. J. Label. Compd. Radiopharm., 50: 375-379, 2007; Wang, C. S., Easwaramoorthy, B., Pichika, R., Collins, D., Head E. and Mukherjee, J. $^{18}$F-FBM: A New PET Radiotracer for Imaging β-Amyloid Plaques and Neurofibrillary Tangles. J. Nucl. Med., 47:217P, 2006; Patel, P. C., Collins, D., Nistor, M., Easwaramoorthy, B., Head, E. and Mukherjee, J.: 18F-Fluoropropylcurcumin: A potential PET tracer for imaging inflammation and A□-plaques. J. Nucl. Med., 48:22P, 2007, all of which are incorporated by reference herein.

Thus, specific embodiments and applications of beta-amyloid and neurofibrillary tangle imaging agents have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A compound having a structure according to Formula I

Formula I wherein Z is C(CN)$_2$ or O;

wherein W is N—Y or CH$_2$, with the proviso that where W is N—Y then n is 1, and with the further proviso that where W is CH$_2$ then n is an integer between 0 and 2;

Y is optionally substituted lower alkyl, optionally comprising a $^{11}$C atom;

R$_1$ is hydrogen, lower alkyl, lower dialkylketone, or substituted aryl;

wherein F is $^{18}$F or $^{19}$F; and wherein X is H, OH, OCH$_3$, OR, SH, SR, NH$_2$, NHR, NR$_2$R$_3$, C(O)R, C(O)OR, or optionally substituted R, wherein R is lower alkyl, and wherein R$_2$ and R$_3$ are independently optionally substituted lower alkyl, or fluoroalkyl.

2. The compound of claim 1 wherein Z is C(CN)$_2$, and wherein R$_1$ is hydrogen, lower alkyl, or lower dialkylketone.

3. The compound of claim 2 wherein F is $^{18}$F or $^{19}$F and Y is CH$_3$.

4. The compound of claim 2 wherein Y is $^{11}CH_3$ and F is $^{19}F$.

5. The compound of claim 2 wherein X is $OH$, $OCH_3$, $SH$, $NH_2$, $NHR_2$, or $NR_2R_3$,
   wherein $R_2$ and $R_3$ are independently optionally substituted lower alkyl.

6. The compound of claim 2 wherein $R_1$ is hydrogen or $CH_2C(O)CH_3$.

7. The compound of claim 1 having a structure according to Formula II Formula II

8. The compound of claim 1 wherein Z is O, and wherein $R_1$ is substituted aryl.

9. The compound of claim 8 wherein $R^1$ is selected from the group consisting of 10. A compound having a structure according to Formula IIa Formula IIa wherein n is an integer between 0 and 4, and wherein X is OH, OR, SH, SR, NH2, NHR, C(O)R, C(O)OR, or optionally substituted R, wherein R is lower alkyl.

11. A pharmaceutical or diagnostic composition comprising the compound of claim 1, or claim 10 and a pharmaceutically acceptable carrier.

12. The pharmaceutical or diagnostic composition comprising the compound of claim 7.

* * * * *